United States Patent [19]

Armstrong et al.

[11] Patent Number: 4,836,904
[45] Date of Patent: Jun. 6, 1989

[54] GRAPHITE ELECTRODE WITH MODIFIED SURFACE

[75] Inventors: Frazer A. Armstrong, Sarah's Cottage; Brian N. Oliver, Chapel Hill; Hugh A. O. Hill, Cumnor, all of United Kingdom

[73] Assignee: Medisense, Inc., Cambridge, Mass.

[21] Appl. No.: 839,699

[22] Filed: Mar. 13, 1986

[30] Foreign Application Priority Data

Mar. 28, 1985 [GB] United Kingdom ................. 8508053

[51] Int. Cl.$^4$ ..................... C25B 11/12; G01N 27/26; A61B 5/04
[52] U.S. Cl. .................................. 204/294; 204/403; 204/290 R; 204/72; 128/639
[58] Field of Search ...................... 204/72, 290 R, 294, 204/400, 1 T, 410, 426, 403; 429/43, 213; 436/101, 102, 113, 63

[56] References Cited

U.S. PATENT DOCUMENTS 4,655,885  4/1987  Hill et al. ......................... 204/290 R
4,711,245 12/1987  Higgins et al. ..................... 128/635

FOREIGN PATENT DOCUMENTS 0108767  5/1984  European Pat. Off. .

OTHER PUBLICATIONS

Malpas (1981), *J. Electroanal. Chem.* 117:347-350.
Malpas (1982), *J. Electroanal. Chem.* 129:1987-1993.

*Primary Examiner*—Barry S. Richman
*Assistant Examiner*—T. J. Wallen

[57] ABSTRACT

An electrode has a graphite surface at least part of which is an edge-plane graphite surface to which Cr(III) complexes are attached by surface C—O groups. The graphite can be polished pyrolytic graphite. The complex coverage can be 5–20%. The complex may comprise proteins, enzyme substrates, specific binding agents, intermediate metabolites or the like, e.g. the protein plastocyanin, so that direct unmediated electrochemistry is possible at the electrode.

8 Claims, 1 Drawing Sheet

GRAPHITE ELECTRODE WITH MODIFIED SURFACE

FIELD OF THE INVENTION

The invention relates to a graphite electrode with a modified surface, to a method of production of such an electrode, and to the use of such an electrode in bioelectrochemistry.

BACKGROUND OF THE INVENTION

Over the last three years it has become known to investigate and exploit redox enzyme systems by electrochemical methods. These involve use of the enzyme and a substrate which is caused to react by the enzyme. The existence or amount of the reaction is measured at an electrode using a mediator compound to transfer electrons from the reaction to the electrode.

A typical example is the system glucose/glucose oxidase/ferrocene (as mediator), as described in commonly owned U.S. Pat. No. 4,711,245 issued on U.S. Ser. No. 607,699, filed May 7, 1984. In a suitable circuit an electrode in contact with such a system will detect a charge, transferred from the enzyme by the mediator. A typical use of such a system is for the selective detection or measurement of blood glucose level in whole blood by an electrode on which layers, or a mixture, of mediator and enzyme are immobilised.

In practice the various components of such a system can be located on the electrode or in the contacting medium; moreover, the system can be used as a test either for substrate or for enzyme or for mediator levels. Elaboration of the basic concepts involves for example the variation of such levels by immunological or nucleic-acid-probe reactions and thus using the system in immunological assay or in DNa/RNA sequencing investigations.

All of the above systems, however, are indirect to the extent that they rely upon a mediator, e.g. ferrocene to transfer the charge from the enzyme molecule to the electrode itself.

SUMMARY OF THE INVENTION

The present invention is concerned with direct electrochemical investigation, where charge is transferred to the electrode without a separate mediator compound.

Graphite is known to possess a "basal plane" surface (in the direction of easy cleavage) and an "edge plane" surface at right angles thereto. Recently, it has been established that electrodes made of pyrolytic graphite and fashioned so as to exhibit an "edge" surface (relative to the graphite structure) give a quasi-reversible electrochemical response with certain electron transfer proteins. Furthermore, this property has been found to be particularly active in those proteins with negatively charged interaction domains in the presence of mobile multivalent cations.

We believe that electrode surface functional groups and where present the mobile ions, promote reversible protein-electrode binding which precedes electron transfer. In certain cases, activity could be clearly identified with the polished edge surface which, unlike the basal plane, possesses a high coverage of carbon-oxygen functionalities including, from chemical analysis, phenolic and carboxylic groups. It is believed that these allow rapid and reversible interaction with the lysine-rich positively-charged haem-edge region of mitochondrial cytochrome c and, accordingly, promote rapid heterogeneous electron transfer. Well-behaved electrochemistry of proteins bearing negatively-charged interaction domains can thus be readily achieved particularly through the inclusion of mobile multivalent cations such as $Mg_{2+}$ and $Cr(NH_3)_6^{3+}$ European patent application No. 0109767 discloses the use of a chemically modified electrode which consists of an electrically conducting pyrolytic graphite substrate with a redox mediator applied to the basal plane thereof. The specification also teaches which mediators can be used in association with the electrode.

The present invention is concerned with modification of an edge-plane electrode surface so that it contains intrinsic positively charged groups.

In one aspect the invention consists in an electrode having a graphite surface at least part of which is an edge-plane graphitic surface to which are attached, by surface carbon-oxygen groups, Cr(III) complexes.

The electrode surface is preferably a polished, or edge-plane, pyrolytic graphite surface, more preferably with a surface coverage of the complex of about 5 to 20%, for example 10%.

The complex is preferably a hexavalent chromium-(III) complex in which some of the ligands comprise the above mentioned functionalities while others comprise chemical specifies selected from the genus comprising: proteins, enzyme substrates, specific binding agents, intermediate metabolites and other physiologically and biochemically active species.

In one particular embodiment, the complex is an ammonia complex of the general formula;

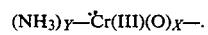

$$(NH_3)_Y\text{---}\overset{..}{C}r(III)(O)_X\text{---}.$$

where "—O" represents oxygen from a surface carbon-oxygen group or from a coordinated water molecule coordinated $H_2O$; and where $X+Y$ equals 6, thereby representing the co-ordination number of the complex.

It is important to appreciate that the electrode of the present invention has linked to its surface certain complexes which are not of themselves mediators, as used in the prior art. The prior art uses separate mediators which may be physically or chemically coated on the electrode or may be dissolved in the solution. In the present invention, however, the complex formation permits reversible binding of the protein and promotes direct electrochemistry.

The modification leads to profound alteration of surface charge characteristics and permits persistent, and well-behaved unmediated electrochemistry of for example the negatively-charged photosynthetic "blue" copper protein plastocyanin, as discussed in more detail below.

The invention further consists in a method of the modification of a graphite electrode at least part of which is an edge-plane graphitic surface, in which the surface is treated with the complex $Cr(NH_3)+++$ in concentrated aqueous ammonia The basis of the modification technique is the rapid formation (via the electrochemical generation of reactive, substitution-labile Cr(II) species) of substitution-inert Cr(III) complexes incorporating electrode surface carbon-oxygen groups. A projected reaction scheme is outlined as shown below, where surface carbon-oxygen functionalities and coordinated $H_2O$ are represented generally as —O.

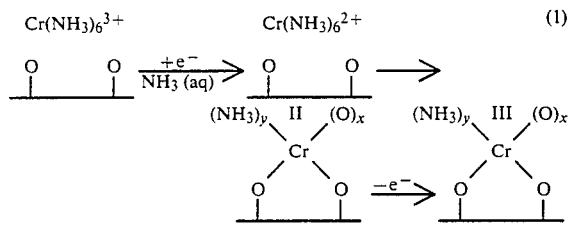

(1)

In the above embodiment the complex $Cr(NH_3)_6^{3+}$ is used, thus permitting surface modification to be carried out in the concentrated aqueous ammonia without complications due to insoluble Cr(III) hydroxy species. The use of aqueous ammonia ensures deprotonation of acidic surface groups, and the competition of $NH_3$ with $H_2O-(OH^-)$ for the remaining chromium coordination sites is believed to minimise extensive formation of lower-charged polymers through olation and oxolation.

In a further aspect the invention consists in a method for direct investigation of the electrochemistry of plastocyanin in which an electrode as defined above is utilised.

The invention will be further described with reference to the following Example read in conjunction with the accompanying drawings.

EXAMPLE

Electrode discs were cut from standard pyrolytic graphite with the a-b (basal) plane perpendicular to the disc face. For examination of protein electrochemistry, a 5 mm disc was sealed in a Teflon electrode sheath. For parallel studies in which modification was examined by X-ray photoelectron spectroscopy, a 9 mm disc was mounted in a PVC girdle and electrical contact was achieved by insertion of a stainless steel needle into the intersection. Spectra were obtained with an ESCALAB 5 spectrometer (VG Scientific, U.K.) with a Mg$_K$ 1.2 excitation source (1253/6 eV).

Plastocyanin is an electron carrier of green-plant chloroplasts which has been isolated as a copper containing protein having a molecular weight of about 11 kD.

Achievement of stable well-behaved electrochemistry of spinach plastocyanin at un-modified edge-oriented pyrolytic graphic electrodes (i.e. subjected only to routine alumina slurry polishing and sonication) normally requires the addition of multivalent cations and reduced temperatures.

At low background electrolyte levels e.g. 5 mM HEPES—1 mM KCl, no electrochemical response is detectable at pH 7; voltammograms are identical to those of buffer alone. This observation is consistent with the expected presence of unshielded coulombic repulsion between protein and electrode. With increased electrolyte levels, e.g. 0.1M KCl, a plastocyanin response is observed but this is poor and short-lived.

Figure 1A:
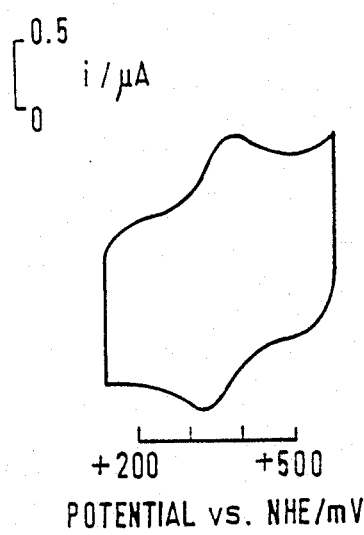
FIG. 1A is DC cyclic voltammogram (20 mV s$^{-1}$ of plastocyanin at a Cr-modified electrode. Pretreatment consisted of a single voltammetric cycle ($-400$, $-1200$ mV) in $Cr(NH_3)_6^{3+}$/aqueous $NH_3$, followed by 4 min. sonication. For clarity, only the fifth scan is shown, Protein concentration is 30 uM in 0.1M KCl, 5 mM HEPES, pH 7.0 Temperature is 20° C.

Following electrode pretreatment by single-scan reductive cycling in a concentrated aqueous ammonia solution of $Cr(NH_3)_6Cl_3$ (typically 20 mM), stable and well-behaved plastocyanin electrochemistry is observed at room temperature, as shown in FIG. 1(A).

The half-wave potential $E_{1/2}$ is $+385$ mV vs. NHE at 20° C., close to potentiometrically determined values and peak separations are typically 60 mV at a scan rate of 20 mV s$^{-1}$. This result is reproducibly obtained upon $Cr(NH_3)_6^{3+}$/aqueous $NH_3$ modification, either by voltammetric cycling (typically one cycle at 20 mV s$^{-1}$, between limits of ca. $-400$ and $-1200$ mV vs. SCE or by poising at a potential of $-1000$ mV or below for ca. 1 minute.

Figure 1B:
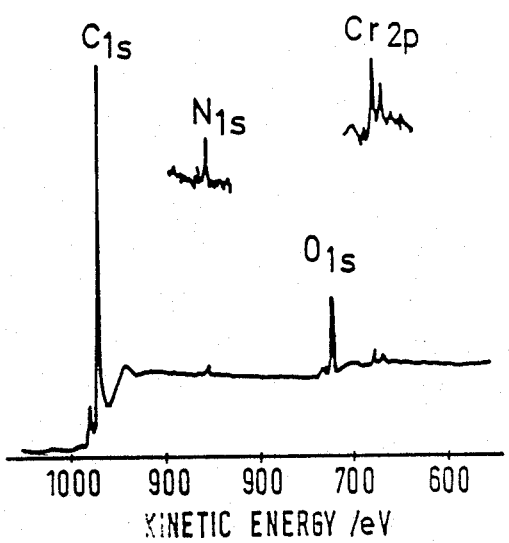

No deterioration of the plastocyanin electrochemical response is evident even after sonicating the modification electrode for 90 minutes. Parallel investigations with ESCA confirm the incorporation of Cr (and N) as further shown in FIG. 1(B). The $Cr_{2p}$ intensity (relative to carbon) is typically consistent with a surface coverage of ca. 10%.

The surface coverage of Cr with respect to C was calculated from the attenuation of photoelectron flux with depth expected for an overlayer of chromium-oxygen, formed on an array of carbon-oxygen groups, at a periodic "edge" lattice structure. An analysis, using estimated ESCA cross sections and mean free paths, was used to derive the approximate coverage.

Figure 2A:
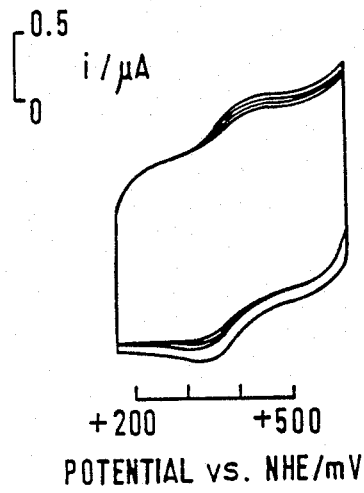
FIG. 2A is a DC cyclic voltammogram (20 mV s$^{-1}$) of plastocyanin at an electrode with which $Cr(NH_3)^{3+}$/aqueous $NH_3$ voltammetric cycling has been restricted ($-400$, $-800$ mv). Conditions are as for FIG. 1A, scans 1-5 are shown. Result is similar to that observed under identical conditions with a routinely polished electrode.
Figure 2B:
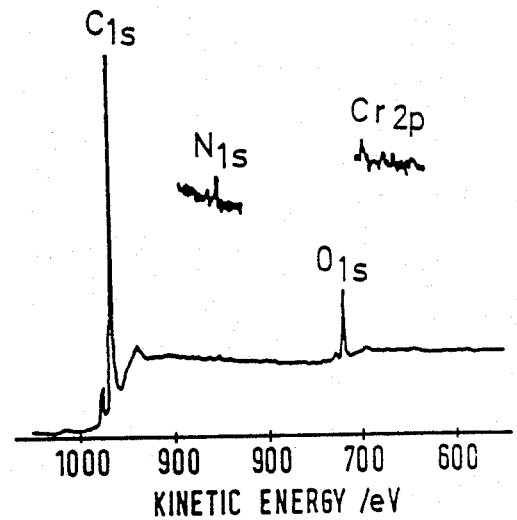
FIG. 2B is a wide scan ESCA spectrum of an edge graphite disc treated identically to FIG. 2A. Scale expansions ($\times 5$) of $Cr_{2p}$ and $N_{1s}$ spectral regions indicate incorporation of small amounts of $NH_3$ but signals in the $Cr_{2p}$ region lie within the noise level.

Control experiments show that restricting potential cycling to the region positive of $-1000$ mv, or cycling in aqueous ammonia alone, gives only an impersistent and rather irreversible plastocyanin response, similar to that obtained for a routinely polished electrode, as shown in FIG. 2(A). The corresponding ESCA spectra, as shown in FIG. 2(B) accordingly shows neglible incorporation of Cr, although there is a small amount of N, most likely representing adsorbed $NH_3$.

The potential threshold for Cr modification, as judged by ESCA and plastocyanin electrochemical activity, lies in the region of $-1000$ mV vs. SCE. This is close to reported values of the polarographic reduction potential for $Cr(NH_3)_6^{3+}$ and corresponds with the appearance of a small cathodic peak at ca. $-1050$ mV in the reduction cycle. It is believed that reduction of $Cr(NH_3)_6^{3+}$ produces labile Cr(II) species, a proportion of which coordinate to surface carbon-oxygen functional groups and undergo rapid reoxidation in view of the observed stability of the surface complexes, it is likely that two or more Cr—O (surface) bonds are involved. The complexes are thus comparable to those implicated in chrome tanning and dyestuffs technology and in chromium polymer derivations of semiconductor surfaces.

As stated above, plastocyanins (MW 10500) from higher plants, transport electrons between photosystems II and I. As a consequence of the significant overall (and conservatively localised) negative charge, physiological and electrochemical activity is highly sensitive to coulombic interactions. Even with low background electrolyte levels, (e.g. 5 mM HEPES 0 1 mM KCl), the chromium-modified electrode is active toward plastocyanin. By contrast, examination of cytochrome c electrochemistry shows clearly marked inhibition of heterogeneous electron transfer as compared with the unmodified edge surface. The response at the Cr-modified electrode is thus consistent with the surface bearing positively charged domains which function to promote reversible binding of plastocyanin prior to electron transfer.

TABLE 1

Cyclic voltammetric and spectroscopic parameters for modified "edge" graphite.

ESCA ANALYSIS

| SAMPLE | Treatment Range | Standardised $C_{1S}$ | Intensity[1] $O_{1S}$ |
|---|---|---|---|
| MODIFIED | Cycle or poise below −100 mV | 7658(969) 8006 | 2439(120) 2190 |
| CONTROL | Cycle or poise in range −400 to −900 mV | 7431 (969) 6484 | 2084(719) 1741 |
| POLISH | — | 7742(969) 8178 | 2574(720) 2013 |

| SAMPLE (NHE) | (Band Energy[2]/ev) | Surface[3] Coverage | FARADAIC RESPONSE WITH PLASTOCYANIN E/p (mV) | $E_{\frac{1}{2}}$ (mV vs. NHE) |
|---|---|---|---|---|
| | | ($N_{1S}$ $Cr_{2p}$ Scan 1(5)) | | |
| MODIFIED | 160(852) 137 | 69c(674, 664) 763 | ca. 10% | 60(60) 60(60) | +387 |
| CONTROL | 74(853) 76 | n.d. n.d. | | 85(>120) | |
| POLISH | n.d. n.d. | n.d. n.d. | — | 100(>130) | |

[1] Band intensities were derived by integration of experimental data and are standardised for the number of scans and the width of scan. Prior to integration, background and satellite structure were substracted. All values are collected for the observed transmission characteristics of the electron emergy analyser.
[2] Typical literature values: $Cr_{2p}$ 673,664 eV; $N_{1S}$ 849 eV
[3] Scan rate 20 mV s$^{-1}$

We claim:

1. An electrode for use in bioelectrochemistry, said electrode comprising:
   (a) a graphite surface, at least part of which is a planar surface at right angles to the direction of easy graphite cleavage; and
   (b) complexes comprising Cr (III), said Cr (III) being attached to said electrode surface by covalent bonds to carbon-oxygen groups, and being capable of attachment by covalent bonds to a ligand that is biochemically active.

2. An electrode as claimed in claim 1 in which the graphite surface is a polished pyrolytic graphite surface.

3. An electrode as claimed in claim 1 having a surface coverage of said complex of from 5% to 20%.

4. An electrode as claimed in claim 1 in which said ligand is a protein.

5. An electrode as claimed in claim 4 in which the protein is plastocyanin.

6. An electrode as claimed in claim 1 in which said ligand is an enzyme substrate.

7. An electrode as claimed in claim 1 in which the electrode is positioned in an aqueous mixture, the complexes having a co-ordination number of six and having the general formula:

$$(NH_3)_Y\text{—Cr(III)—}(O)_X\text{—}$$

where —O represents oxygen from one said carbon-oxygen groups or from a water molecule from said aqueous mixture which is coordinated to the complexes, and where $X+Y=6$.

8. An electrode as claimed in claim 1 in which the electrode is adapted to be positioned in an aqueous mixture, the Cr (III) having a coordination number of six and being part of a complex having the general formula:

$$(NH_3)_Y\text{—CR(III)—}(O)_X\text{—}$$

where $X+Y=6$, and where —O represents oxygen atom(s) at least one of which is from one of said carbon-oxygen groups and the remainder of which are from a water molecule from said aqueous mixture coordinated with said Cr (III), or are from one of said carbon-oxygen groups.

* * * * *